United States Patent [19]
Shartava

[11] Patent Number: 6,020,120
[45] Date of Patent: Feb. 1, 2000

[54] USE OF N-ACETYLCYSTEINE TO STORE RED BLOOD CELLS AND A METHOD OF AGING RED CELLS WITH NITROGEN

[75] Inventor: Archil Shartava, Mobile, Ala.

[73] Assignee: South Alabama Medical Science Foundation, Mobile, Ala.

[21] Appl. No.: 08/955,823

[22] Filed: Oct. 22, 1997

[51] Int. Cl.$^7$ .............................. A01N 1/02; A01N 63/00; A01N 37/12

[52] U.S. Cl. ............................ 435/2; 424/93.73; 514/562

[58] Field of Search ............................... 435/2; 424/93.73; 514/562

[56] References Cited

PUBLICATIONS

Horinaka et al., "Protection of Cellular alpha Tocopherol by Intracellular Glutathione in Human Erythrocytes", Dokkyo J. Med. Sci. 19 (2) : 75–85 (1992).

Runge–Morris et al., "Differential Effects of Organic Hydroperoxides and Hydrogen Peroxide on Proteolysis in Human Erythrocytes", Chemical Research in Toxiodolgy 2 (2) : 76–83 (1989).

Spooner et al., "Heat Stability and Kinetic Properties of Human Serum Glutathione Reductase Activity in Various Disease States", Biochem. Med. 26 (2) : 239–48 (1981).

Mazor et al., "Red Blood Cell Permeability to Thiol Compounds", Eur. J. Haemoatol. 57 (3) : 241–246 (1996).

Lachant et al., "Antioxidant Metabolism during Blood Storage and Its Relationship to Postrransfussion Red Cell Survival", American J. Hematology 17 (3) : 237–49 (1984).

Knight and Searles, Annals of Clinical and Laboratory Science 24:294–301 (1994).

*Primary Examiner*—Sandra E. Saucier
*Attorney, Agent, or Firm*—Braman & Rogalskyj, LLP

[57] ABSTRACT

The invention provides a method of preserving red blood cells. The method comprises treating the red blood cells with about 2 mM to about 35 mM of N-acetylcysteine. The invention further provides a method of aging red blood cells. This method comprises isolating red blood cells; incubating the isolated red blood cells at about 37° C.; and cyclically exposing the incubated red blood cells to $N_2$ for about 15 minutes then to ambient air for about 5 minutes for a total of about 16 hours. This method allows for the timely screening of agents for their ability to affect the premature aging of red blood cells. This timely screening can be conducted in the course of 16 hours as opposed to weeks or months that would be necessary if the red cells could not be prematurely aged in accordance with the method of the subject invention.

3 Claims, 2 Drawing Sheets

USE OF N-ACETYLCYSTEINE TO STORE RED BLOOD CELLS AND A METHOD OF AGING RED CELLS WITH NITROGEN

FIELD OF THE INVENTION

The subject invention is directed generally to the preservation of blood, and more particularly to a method of preserving red blood cells by treating them with N-acetylcysteine.

BACKGROUND OF THE INVENTION

Throughout this application various publications are referenced, many in parenthesis. Full citations for each of these publications are provided at the end of the Detailed Description. The disclosures of each of these publications in their entireties are hereby incorporated by reference in this application.

Transfusion therapy worldwide relies on the availability of fresh and viable red blood cells (also known as erythrocytes). Red blood cells from various donor sources can be packaged and stored for future use in transfusion therapy. The shelf life and viability of the stored red blood cells has a great impact on how many of these packaged cells are wasted, since non-viable or expired red blood cells must be discarded.

As early as 1947, attempts to prolong the shelf life of packaged red blood cells have been made. These attempts began with the use of the nutrient-anticoagulant solution acid-citrate-dextrose (ACD) for the preservation of whole blood (Gibson et al. 1947; Ross et al. 1947). Gibson et al. (1957) later reported that blood stored in citrate-phosphate-dextrose (CPD) was more stable than blood stored in ACD. Storage at 4° C. and the addition of 0.25 mM adenine further increased the viability and storage time of red blood cells (Valeri and Zaroulis 1972; Kreuger et al. 1975). Addition of citrate-phosphate-dextrose-adenine solution, with additional added glucose (CPDA-1), thus became the preferred method for increasing the storage time of red blood cells.

Attempts at further improvements in the storage time of red blood cells began to focus on lipid peroxidation (Hochstein and Jain 1981). Lipid peroxidation is the oxidative deterioration of polyunsaturated fatty acids in cell membranes, and is a widely accepted mechanism for cellular injury and death (Gutteridge and Quinlan 1983; Halliwell 1984; Halliwell and Gutteridge 1984).

Lee (1980) reported that the addition of reduced glutathione (GSH), a naturally occurring antioxidant, and ethylenediaminetetraacetic acid (EDTA), an effective metal chelating agent, significantly reduced lipid peroxidation in plasma stored at 4° C. to 5° C. The addition of both agents resulted in additive reduction in lipid peroxidation. Knight et al. reported that the addition of various metal binding chelators to both irradiated (Knight et al. 1992a) and non-irradiated (Knight et al. 1992b; Knight et al. 1992c) blood resulted in significantly reduced lipid peroxidation levels. Oral supplementation with vitamin C and E, well-accepted free radical scavengers, also resulted in decreased lipid peroxidation in both irradiated and non-irradiated red blood cells (Knight et al. 1993).

Knight and Searles also tested the effects of a variety of other antioxidants on lipid peroxidation in stored blood in an attempt to define other possible agents that might improve red cell life-span of transfused blood (Knight and Searles 1994). These other antioxidants included the metal chelator phytic acid, the transition metal ions zinc (II) and manganese (II), and the free radical scavengers quercetin, N-acetylcysteine, mannitol, uric acid, and 1,3-dimethyluric acid. In this study, Knight and Searles used a 1.0 mM preparation of N-acetylcysteine (NAC) and concluded that NAC was mildly effective at reducing lipid peroxidation in stored whole blood after 7 and 14 days, but was not significantly different from controls on day 18. In view of these results and the results with the other antioxidants tested, Knight and Searles concluded that all of the antioxidants studied, except phytic acid and possibly urate and NAC, might be useful either alone or in combination with other selected agents in increasing red cell life-span and extending allowable storage time prior to transfusion.

In view of the massive amounts of packaged red blood cells used in transfusion therapy today worldwide, a need continues to exist for additional and better ways to prolong the shelf life and viability of the stored red blood cells. Increased shelf life and prolonged viability has a great impact on how many of these packaged cells are wasted, since non-viable or expired red blood cells must be discarded.

SUMMARY OF THE INVENTION

The subject invention addresses this need by providing a method of preserving red blood cells. The method comprises treating the red blood cells with about 2 mM to about 35 mM of N-acetylcysteine.

The invention further provides a method of aging red blood cells. This method comprises isolating red blood cells; incubating the isolated red blood cells at about 37° C.; and cyclically exposing the incubated red blood cells to $N_2$ for about 15 minutes then to ambient air for about 5 minutes for a total of about 16 hours. This method allows for the timely screening of agents for their ability to affect the premature aging of red blood cells. This timely screening can be conducted in the course of 16 hours as opposed to weeks or months that would be necessary if the red cells could not be prematurely aged in accordance with the method of the subject invention.

BRIEF DESCRIPTION OF THE DRAWINGS

These and other features and advantages of this invention will be evident from the following detailed description of preferred embodiments when read in conjunction with the accompanying drawings in which.

DETAILED DESCRIPTION OF THE INVENTION

Figure 1A:
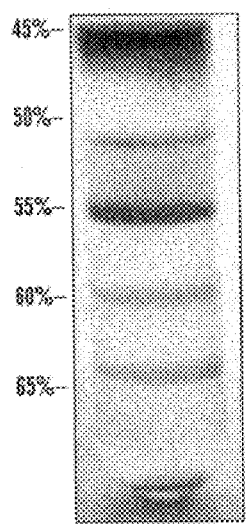
FIGS. 1A–1D illustrate the formation of dense cells from normal red blood cells under different conditions.
Figure 1B:
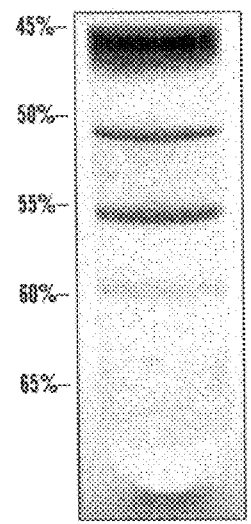
Figure 1C:
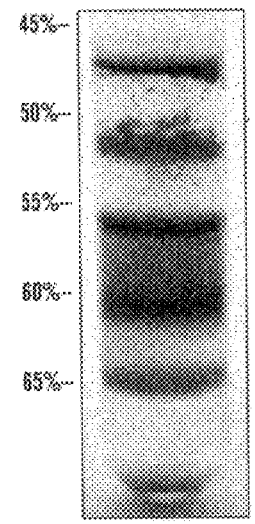
Figure 1D:
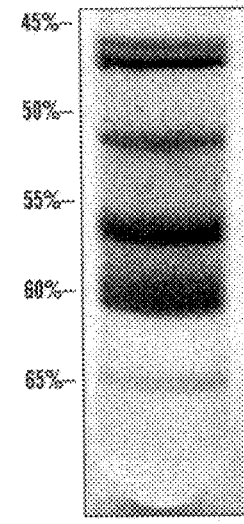

The subject invention provides a method of preserving red blood cells (RBCs). The method comprises treating the red blood cells with about 2 mM to about 35 mM of N-acetylcysteine (NAC). Treatment with about 10 mM to about 20 mM of NAC provides the best preservation of RBCs.

As used herein, "preserving" refers to prolonged viability and shelf-life of stored (packaged) red blood cells. The viability and shelf-life of RBCs is determined by measuring the formation of dense cells. During the aging of human red blood cells, the cells become more dense and can be separated from young cells on a density gradient. Therefore, reduction in the formation of dense cells can be used as an indicator of increased viability and shelf-life; in other words, as an indicator of RBC preservation.

As further used herein, N-acetylcysteine (NAC) refers to L-α-acetamido-β-mercaptopropionic acid (see Smith and Gorin 1961 for preparation of NAC; see also the Merck Index entry for acetylcysteine).

As further used herein, "treating" the red blood cells refers to exposure of the red blood cells to NAC. This exposure can be accomplished, for example, by taking a sample of RBCs and adding to the sample a solution of NAC for a final concentration of NAC of about 2 mM to about 35 mM. "About" as used herein refers to an amount that is near to the stated amount by relative amounts. For a small amount such as 2 mM, an amount of about 2 mM would require that the amount be within small fractions of 2. For example, although 1 mM is only 1 mM different from 2 mM, 1 mM is not about 2 mM since there is a 2× difference in concentration between 1 mM and 2 mM. For a large amount such as 35 mM, however, an amount of about 35 mM would only require that the amount be within a few mM of 35. For example, 34 mM is 1 mM different from 35 mM which in relative terms (1 out of 34 or 35) is near.

The invention further provides a method for aging red blood cells. Such a method is useful in the screening of various agents for their effect on the aging of RBCs. As discussed above, the formation of dense cells is an indicator of red blood cell aging. A decrease in the formation of dense cells as a result of the treatment of RBCs with an agent is an indication that the agent is useful for preserving red blood cells. Generally, the aging of red blood cells can take weeks. Therefore, the screening of agents for their effect on the RBC aging process would also take weeks. The method of the subject invention significantly shortens this time period to about 16 hours.

The method of aging red blood cells comprises isolating red blood cells; incubating the isolated red blood cells at about 37° C.; and cyclically exposing the incubated red blood cells to $N_2$ for about 15 minutes then to ambient air for about 5 minutes for a total of about 16 hours. This treatment results in the formation of dense cells. An agent can be screened for its ability to decrease the formation of dense cells by introducing the agent into the incubated red blood cells prior to the cyclical exposure to $N_2$ and ambient air. If the formation of dense cells is decreased by the agent, the agent is a suitable agent for the preservation of red blood cells.

EXAMPLE I

In this experiment, normal blood was separated into two equal parts. One part served as a control and was kept at 4° C. for 15 days. The second part was treated with 20 mM NAC and kept at 4° C. for 15 days as well. After 15 days of incubation, 1 ml of each blood was placed over a discontinuous Percoll density gradient (in centrifuge tubes) contain each of 45%, 50%, 55%, 60% and 65% Percoll in 18% Renografin M-60 and 20 mM Hepes, 10 ml $MgCl_2$, 1 mM glucose, pH 7.4. The blood was sedimented at 907×g for 45 minutes at 4° C. and tubes were photographed after centrifugation. Each layer of blood created after centrifugation was removed without cross contamination. The cells were washed two times in PBS (10 mM $NaPO_4$, 150 mM NaCl, pH 7.4) and the number of RBCs was counted.

The formation of dense cells from normal RBCs during incubation at 4° C. for 15 minutes was quite pronounced. Dense cells were considered to be those cells which migrated on a Percoll gradient to layers below 50% Percoll, i.e. to 55%, 60% and 65% Percoll. 20 mM NAC significantly reduced (>50%) the formation of these dense cells.

EXAMPLE II

A 2% suspension of normal RBCs was prepared in incubation buffer (IB)(20 mM Hepes, 130 mM NaCl, 5 mM KCl, 1 mM $MgCl_2$, 1 mM glucose, 2 mM $NaPO_4$, 2 mM $CaCl_2$, 1 mM adenosine, 0.5% BSA, 100 units Penicillin G, 100 μg Streptomycin, 0.25 μg Amphotericin B, pH 7.4). Two equal samples of this suspension were obtained. One sample served as a control and the second was treated with 20 mM NAC. The method of $N_2/O_2$ cycling was utilized for both samples to age the RBCs. After that the samples were analyzed as in Example I.

In the control sample, a significant amount of red cells migrated to 60%, 65% Percoll and below. 20 mM NAC was extremely effective in reducing the formation of dense cells. Overall more than 5 times less the amount of dense cells were produced in the presence of 20 mM NAC. Formation of very dense cells (65% and >65% Percoll) was almost totally eliminated.

EXAMPLE III

In this experiment, low density and high density cell suspensions were prepared. Intact blood was placed over Percoll density gradients and low density (45% Percoll) and high density (>45% Percoll) cells were obtained. A 2% suspension of both fractions was prepared in incubation buffer (IB), and the remainder of the procedure was as described in Example II. The result of this experiment after centrifugation is shown in FIG. 1.

Referring to FIG. 1, normal erythrocytes were separated in two fractions: low and high density. Cells from both fractions were repeatedly oxygenated/deoxygenated during 16 hours to create new aged dense cells. After that initially low density cells and high density cells were separated on the gradients (FIGS. 1A and 1B—low density; FIGS. 1C and 1D—high density). During this experiment, fractions 1B and 1D contained 20 mM NAC. As shown in FIGS. 1A–1D, those fractions which were treated with NAC generated significantly less dense cells (lanes 60%, 65% and the bottom of each tube).

EXAMPLE IV

In this experiment, five different concentrations of NAC (0.5 mM, 5 mM, 10 mM, 20 mM and 50 mM) were used to determine the range of efficacy of NAC to protect red blood cells against oxidative damage. The method as described in Example II was used with the substitution of the desired concentration of NAC.

Figure 2:
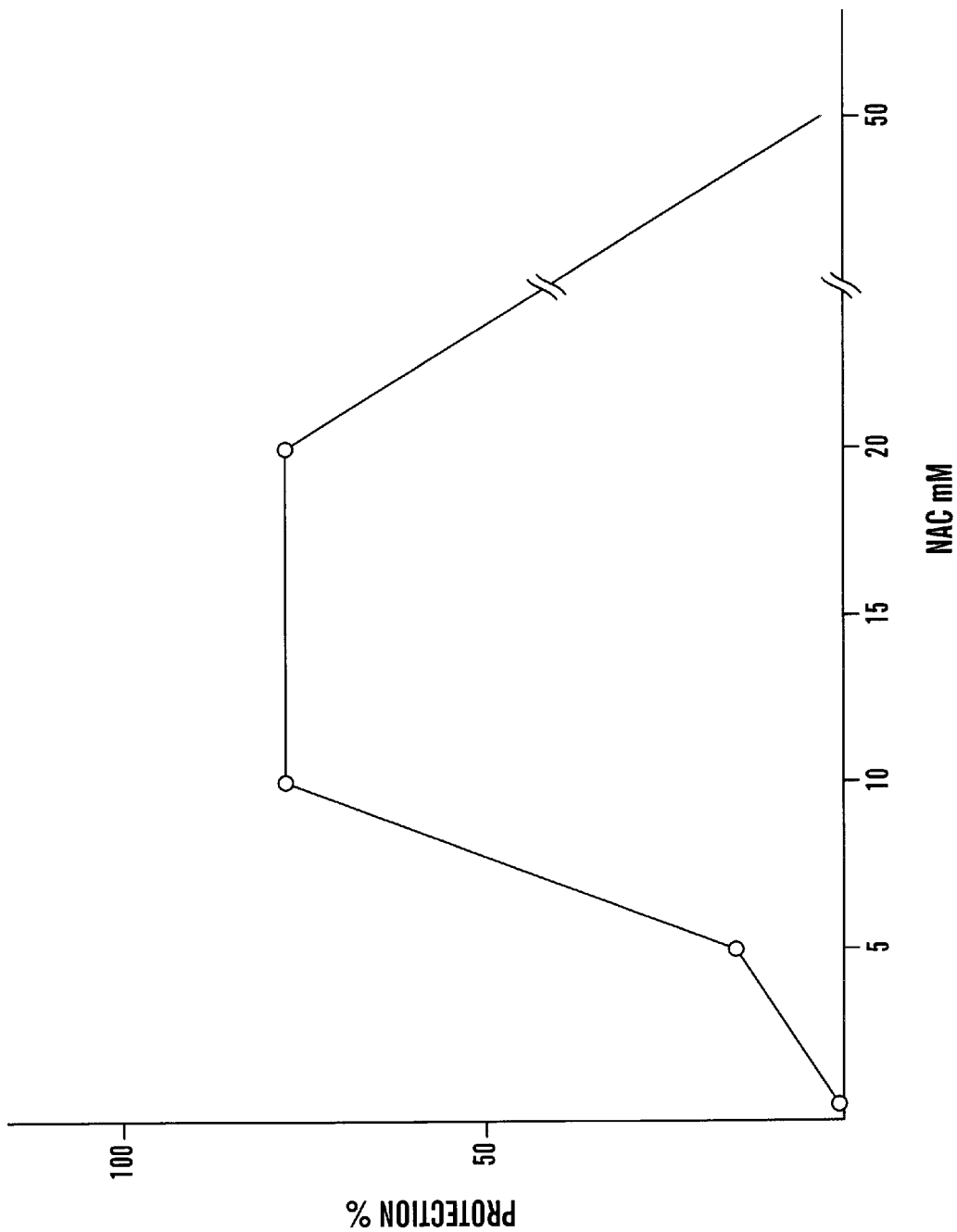
FIG. 2 illustrates the protective effect (in %) of different concentrations of NAC against the generation of dense cells.

The effective range of NAC for reduction of dense cell formation was between 2 mM and 35 mM. At concentrations above 25 mM, RBCs began undergoing hemolysis. The protective effect (in %) of different concentrations of NAC against generation of dense cells is shown in FIG. 2.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

REFERENCES

Gibson, J. C., et al., J Clin Invest 26:715–738 (1947).
Gibson, J. C., et al., Am J Clin Pathol 28:569–578 (1957).

Gutteridge, J. M. C., and Quinlan, G. T., J Appl Biochem 5:293–299 (1983).
Halliwell, B., Med Biol 52:71–77 (1984).
Halliwell, B., and Gutteridge, J. M. C., Biochem J 219:1–14 (1984).
Hochstein, P., and Jain, S. K., Fed Proc 40:183–188 (1981).
Kreuger, A., et al., Vox Sang 29:81–89 (1975).
Lee, D. M., Biochem Biophys Res Com 95:1663–1672 (1980).
Knight, J. A., et al., Ann Clin Lab Sci 22:417–422 (1992a).
Knight, J. A., et al., Transfusion 32:353–357 (1992b).
Knight, J. A., et al., Ann Clin Lab Sci 22:207–213 (1992c).
Knight, J. A., et al., Ann Clin Lab Sci 23:51–56 (1993).
Knight, J. A., and Searles, D. A., Annals of Clinical and Laboratory Science 24(4):294–301 (1994).
The Merck Index, 12th Edition, Budavari, S., Editor, Merck & Co., Inc., Whitehouse Station, N.J., pp. 16, entry #89 (1996).
Ross, J. F., et al., J Clin Invest 26:687–703 (1947).
Smith and Gorin, J Org Chem 26:820 (1961).
Valeri, C. R., and Zaroulis, C. G., New Engl J Med 267:1307–1313 (1972).

What is claimed is:

1. A method of aging red blood cells which comprises:
isolating red blood cells;
incubating the isolated red blood cells at about 37° C.; and
cyclically exposing the incubated red blood cells to $N_2$ for about 15 minutes then to ambient air for about 5 minutes for a total of about 16 hours.

2. A method of preserving red blood cells comprising:
providing red blood cells;
treating red blood cells with about 2 mM to about 35 mM of N-acetylcysteine; and
storing the treated red blood cells for more than 15 days.

3. A method according to claim 2, wherein the red blood cells are treated with from about 10 mM to about 20 mM of N-acetylcysteine.

* * * * *